United States Patent [19]

Gross et al.

[11] 4,405,312
[45] Sep. 20, 1983

[54] CONNECTING DEVICE FOR MEDICAL LIQUID CONTAINERS

[75] Inventors: James R. Gross, Bartlett; Mark E. Larkin, Lindenhurst, both of Ill.

[73] Assignee: Abbott Laboratories, North Chicago, Ill.

[21] Appl. No.: 298,049

[22] Filed: Aug. 31, 1981

[51] Int. Cl.³ .............................................. A61M 3/00
[52] U.S. Cl. .................................... 604/29; 604/283; 604/905
[58] Field of Search ............... 128/247, 214 R, 214 G, 128/214 F, 215, 214.2, 334 C, 213 A; 251/149.1, 149.9; 285/DIG. 2, 260, 38, 27, 45, 373, 423, 21, 419; 215/249, 251, 274, 247; D3/50; 604/27-29, 280, 283, 403, 408, 411, 412, 415, 905

[56] References Cited

U.S. PATENT DOCUMENTS

| | | | |
|---|---|---|---|
| D. 110,184 | 6/1938 | Lobel | D3/50 |
| D. 122,146 | 8/1940 | Moore | D3/50 |
| 3,311,396 | 3/1967 | Hotchkiss et al. | |
| 4,043,333 | 8/1977 | Munsch | 128/214 G |
| 4,201,406 | 5/1980 | Dennehey et al. | |
| 4,209,013 | 6/1980 | Alexander et al. | 128/247 X |
| 4,286,640 | 9/1981 | Knox et al. | 215/249 X |
| 4,296,949 | 10/1981 | Muetterties et al. | 604/905 X |
| 4,340,052 | 7/1982 | Dennehey et al. | 128/247 |

*Primary Examiner*—Richard J. Apley
*Assistant Examiner*—Michelle N. Lester
*Attorney, Agent, or Firm*—Robert S. Beiser; Robert L. Niblack

[57] ABSTRACT

A connecting device for medical liquid administration sets, particularly for use in continuous ambulatory peritoneal dialysis comprises a tubular port extending from a medical liquid container. The tubular port has a pierceable diaphragm positioned within and sealing the same. A hollow tubular piercing pin having a sharpened tip is used for penetrating the pierceable diaphragm. A length of flexible tubing extends from the piercing pin and is connected to a catheter positioned in the peritoneum of the patient once the piercing pin and port are connected. A locking mechanism is utilized for selectively retaining the piercing pin within the tubular port following insertion, and for asepticizing the connection.

21 Claims, 25 Drawing Figures

CONNECTING DEVICE FOR MEDICAL LIQUID CONTAINERS

BACKGROUND OF THE INVENTION

The present invention relates generally to the field of connecting mechanisms for fixedly joining together a length of tubing to a medical liquid container. Connectors of this general type are capable of a wide variety of uses in medical applications. The connector of the present mechanism was developed specifically for use in continuous ambulatory peritoneal dialysis.

Prior to the present invention, connectors of this general type have been used for many years to effectuate rapid and effective junctions between pieces of tubing. A requirement of such connectors is that a fluid-tight seal be obtained. Another requirement is that the connection, once made, should be strongly resistant to inadvertent disengagement, but should be readily disengageable when desired by simple and rapid manual manipulation.

It has long been known that fluid-tight connections are provided by a pair of tapered members, one including a female portion having an internal opening with an inner conical tapered sealing surface, and the other member including a male portion having a protrusion with an outer concial, matingly tapered, sealing surface. However, in order to ensure the desired fluid-tight connection, the members must be forced longitudinally together, preferably with a slight twisting motion, with sufficient pressure to ensure that the locking friction angle of the tapered surfaces are jammed into intimate frictional contact. Even when the desired intimate contact providing the fluid-tight connection is established, an inadvertent, longitudinal tugging between the tubes associated with the two members is often sufficient to disengage the connection and break the seal.

Similarly, the use of piercing pins adapted for connection to medical liquid containers is commonly known in the art. However, such piercing pins are commonly inserted into a length of flexible tubing extending from the containers in a press-fit connection which is difficult to disengage while in use. Thus, the problem heretoforce unsolved by the prior art is the provision of simplified means to ensure the intimate frictional contact sufficient to provide fluid-tight connection and to preclude relative longitudinal motion tending accidentally to disengage the sealing surfaces, while at the same time allowing selective disengagement with relatively easy manual manipulation. At the same time, maintaining the connection in an aseptic condition is also desirable.

Examples of attempts to overcome this problem are the devices shown in U.S. Pat. Nos. 4,201,406; 4,030,494; and 229,518. In regard to the '406 patent, the present disclosure has the following advantages:

1. No pocket or hole for germs to grow in;
2. Can be opened for cleansing;
3. Replaced after each use;

In addition, in Preferred Embodiment A, one hand unlatch/removal feature latching means may be found. Despite these efforts in the field of peritoneal dialysis, a relatively high rate of peritonitis has been found, which, it is suspected, is due to the passage of microorganisms through the connector and into the peritoneal cavity of the patient. In order to prevent such microbial contamination, it is an advantage of the present invention to provide a novel connecting device which maintains the connection between a piercing pin and a container port in a sealed configuration. As an additional feature, the present connector may include an aseptic barrier positioned within the device which provides a barrier against the invasion of microbial contaminants. It is an additional advantage of the present invention to provide such a connecting device which is relatively easy to manipulate and inexpensive to manufacture.

SUMMARY OF THE INVENION

The foregoing advantages are accomplished and the shortcomings of the prior art are overcome by the connecting device of the present invention, which comprises a tubular port member extending from a medical liquid container and having a pierceable diaphragm positioned within and sealing said port member. A hollow tubular piercing pin connected to a length of flexible tubing at its proximal end and having a sharpened tip at its distal end is adapted for penetrating the pierceable diaphragm. A locking mechanism is provided for selectively retaining the piercing pin within the tubular port member following such insertion.

The tubular port member perferably includes a rigid tubular insert fixedly attached within and sealing the port. The rigid tubular insert has a circular flange extending concentrically therefrom which is designed to limit the insertion of the plug into the tubular port. Additionally or alternatively, the tubular port itself may include a concentric circular flange disposed about its distal end, adapted for connection to the locking mechanism previously metioned. The tubular piercing pin also includes a similar circular flange for limiting the insertion of the piercing pin into the port.

The previously mentioned locking mechanism comprises a clasp member composed of first and second C-shaped portions, hingedly connected together. Each of the C-shaped members include oppositely disposed semicircular slots adapted for reception of and engagement with the tubular port or alternatively, the piercing pin. The C-shaped portions of the clasp also include a latching mechanism so that when the clasp member is pivotally enclosed about the connection between the pin and the port, the latch may be closed and locked. The clasp mechanism is designed to engage with the previously mentioned circular flanges so that the piercing pin and the port may not be moved longitudinally out of the clasp. As a result, the connecting device fixedly positions the piecing pin relative to the tubular port.

An additional feature of the clasp mechanism is in inclusion of antiseptic sponges or another absorbent medium in each of the C-shaped portions, constructed and arranged for asepticizing the connection between the tubular port and the piercing pin. This is accomplished by means of an antiseptic solution dispensed into the sponge, such as povidone iodine (Betadine). Other commonly known antiseptic solutions may also be used.

The invention further includes a method of aseptically sealing the connection between the piercing pin and the tubular port of a medical liquid container. The method comprises the steps of inserting the pin into the port, piercing the diaphragm of the port with the pin and enclosing the assembled port and pin within a clasp mechanism having a plurality of sponge members therein saturated with antiseptic solution. In a preferred embodiment, the clasp mechanism comprises a modular unit constructed of injection molded polypropylene or other thermoplastic propylene having an integrally formed flexible hinge between the first and second portions. The latch mechanism comprises an integrally formed latch on one of the C-shaped members and a slot constructed and arranged for reception of the latch on the opposing C-shaped member so that when the two C-shaped members are pivoted towards each other, the latch may be engaged into the opposing slot. The latch mechanism may also be selectively disengaged, as required. Disengagement is accomplished with one hand using the thumb and forefinger moving in opposite directions to simultaneously disengage the latches. Another advantage of this latch system is that accidental disengagement of the latches is unlikely since opposite direction forces acting on the latch tabs is required. One latch can be disengaged without the clamshell opening.

In a preferred embodiment, a lock nut is used to connect the clasp mechanism to the bag port. The lock nut:
1. Acts as large, comfortable grip for holding port and removing pin while pin is inserted;
2. Mechanically seats pin in port;
3. Mechanically retains port to pin;
4. Prevents the clasp from disengaging from pin, even if both latches are accidentally disengaged.

DETAILED DESCRIPTION OF THE PREFERRED EMBODIMENT

While this invention is susceptible of embodiment in many different forms, there is shown in the drawings and will herein be described in detail, several specific embodiments, with the understanding that the present disclosure is to be considered as an exemplification of the principles of the invention and is not intended to limit the invention to the embodiments illustrated.

Figure 1:
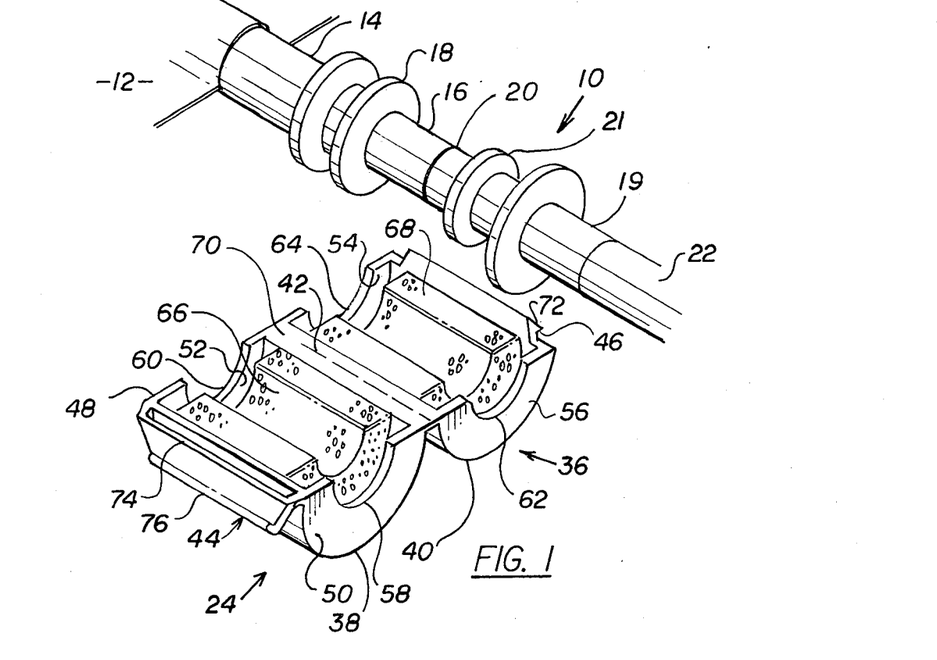
FIG. 1 of the drawings is a front perspective view of an improved connecting device for medical liquid containers.
Figure 2:
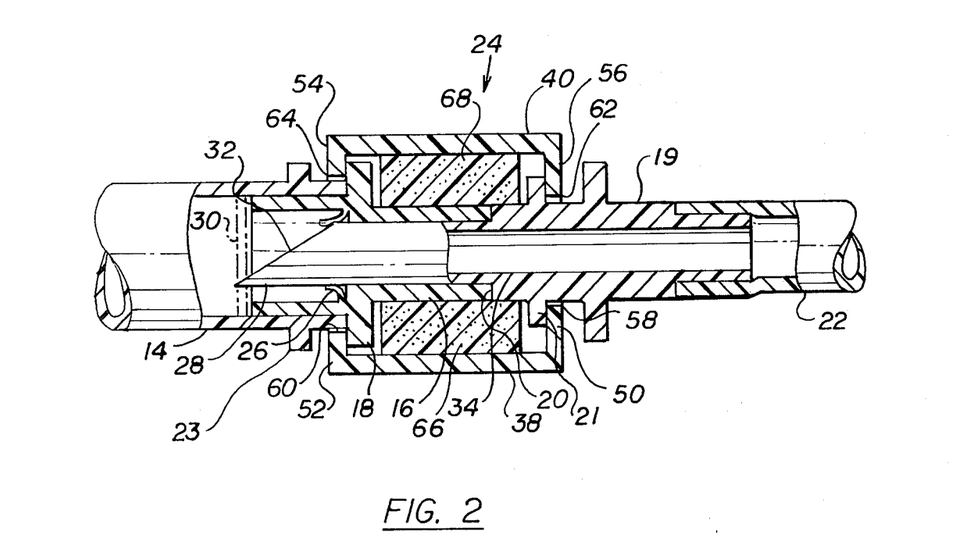
FIG. 2 of the drawings is a view in vertical section of the improved connecting device of FIG. 1 shown in a connected position.

As best seen in FIGS 1 and 2 of the drawings, improved connecting device 10 for medical liquid container 12 connects a tubular port 14 extending from container 12. Extending from tubular port 14 is a rigid tubular insert 16 having a radial flange 18 concentrically disposed therearound, adapted for limiting the insertion of insert 16 into port 14. In order to provide access to liquid in container 12, a piercing pin 19 extends into tubular insert 16. Piercing pin 19 has a shoulder 20 concentrically disposed therearound and adapted for limiting the insertion of piercing pin 19 into insert 16. A length of flexible tubing 22 extends from piercing pin 19 and is adapted for the conveyance of liquid. Once piercing pin 19 is inserted into rigid tubular insert 16 and hence into tubular port 14, locking mechanism 24 may be utilized to retain piercing pin 19 within tubular port 14.

As best seen in FIG. 2, disposed within tubular insert 16 is a pierceable diaphragm 26 which is penetrated by sharpened tip 28 of piercing pin 19 upon insertion into tubular port 14. Following such insertion, medical liquid contained within container 12 may pass from container 12, through tubular port 14, piercing pin 19, and out flexible tubing 22. Further seen in the drawings is radial circular flange 23 extending concentrically from tubular port 14 and adapted, with circular flange 18, for positioning locking means 24 relative thereto. Tubular port 14 may also include a pierceable diaphragm 30 disposed therein and adapted for sealing of the port until penetration by piercing pin 19. In order to allow the flow of liquid through piercing pin 19, sharpened tip 28 has an open orifice 32 proximate thereto and opening into lumen 34 extending through piercing pin 19.

Returning to FIG 1 of the drawings, locking mechanism 24, in a preferred embodiment, comprises a clasp member 36 which comprises first C-shaped portion 38 and second C-shaped portion 40, hingedly connected along midline 42 and including latching mechanism 44 at opposing ends 46 and 48. Clasp member 36 is constructed and arranged for pivotal enclosure of connecting device 10 and for the fixed position of piercing pin 19 relative to tubular port 14. A key aspect of the design of clasp 36 is the inside diameter of C-shaped members 38 and 40 which are of sufficient size to receive circular flanges 18 and 21 and to prevent them from being longitudinally displaced. In order to accomplish this, end walls 50, 52, 54 and 56 extend downwardly from the outside surface of clasp 36 to enclose flanges 18 and 21. In addition, in order to allow the extension of tubular port 14 and flexible tubing 22 from clasp member 36, semicircular slots 58, 60, 62 and 64 are oppositely disposed on first portion 38 and second portion 40 of clasp member 36. Thus, when clasp member 36 is pivotally enclosed about connecting device 10, semicircular slots 58 and 62 are radially disposed about flexible tubing 22. Similarly, semicircular slots 62 and 64 are radially disposed about tubular port 14. A clamshell effect is thereby obtained.

As an additional feature, as best seen in FIG. 1, antiseptic sponge members 66 and 68 are positioned within first C-shaped portion 38 and second C-shaped portion 40. In a preferred embodiment, sponge members 66 and 68 are C-shaped and are adhesively attached to their respective C-shaped portions. Contained within sponge members 66 and 68 is an antiseptic solution such as povidone iodine (Betadine).

When clasp member 36 is enclosed about connecting device 10, the antiseptic solution disposed within sponges 66 and 68 serves as a sterile barrier to the invasion of microbes. While the clasp member 36 is designed specifically for use with tubular ports and piercing pins having circular flanges such as 18 and 20, clasp 36 may be used for any conventional I.V. bag connection to provide an aseptic covering of the connection therebetween.

As further seen in FIG. 1, clasp member 36 preferably comprises a modular unit constructed of an injection molded plastic such as polypropylene or other commonly known medical plastics and having an integrally formed hinge 70 between first portion 38 and second portion 40. Latching mechanism 44 preferably comprises a male latch member 72 extending from C-shaped portion 40 and a female slot member 74 extending radially from C-shaped portion 38. When first C-shaped portion 38 is pivotally rotated relative to seocond C-shaped portion 40, male latch 72 engages female slot member 74 so as to lock in a closed position until release is desired. However, other commonly known hinges and latch mechanisms may be employed, as well as any suitable medical grade plastic material.

The invention also includes a method of aseptically sealing the connection between a piercing pin and a tubular port of a medical container. The method comprises the steps of inserting piercing pin 19 into tubular port 14. Piercing pin 19, by means of sharpened tip 28, pierces diaphragm 26 within tubular port 14. Once the connection is made, the assembled tubular port and piercing pin are enclosed with a clasp mechanism 36 having sponge members 66 and 68 contained therein which are saturated with an antiseptic solution.

Figure 3:
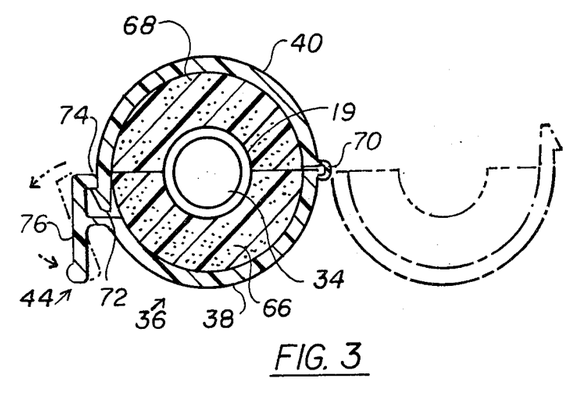
FIG. 3 of the drawings is a view in vertical section of the connecting device shown in FIG. 2.

A cross-sectional view of FIG. 2 may be found in FIG. 3 of the drawings. As described previously, clasp member 36 is pivotally enclosed about piercing pin 19, which has lumen 34 extending therethrough. Latching mechanism 44 comprises male and female members 72 and 74 adapted for joinder together. Pivot arm 76 is used to distort member 74, therby allowing release of member 72 and re-opening of clasp 36 as required.

Figure 4:
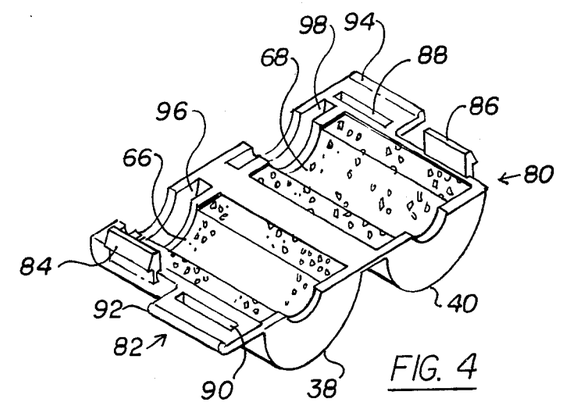
FIG. 4 of the drawings is a front perspective view of an alternative embodiment of the connecting device of this invention.
Figure 5:
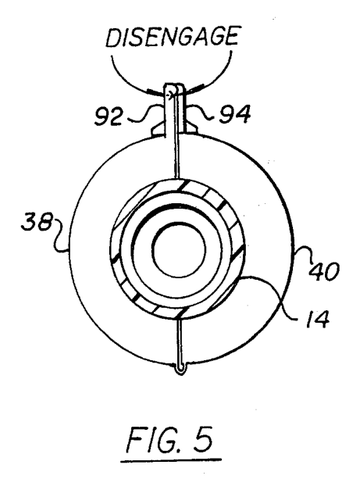
FIG. 5 of the drawings is a front view of the connecting device shown in FIG. 4.
Figure 6:
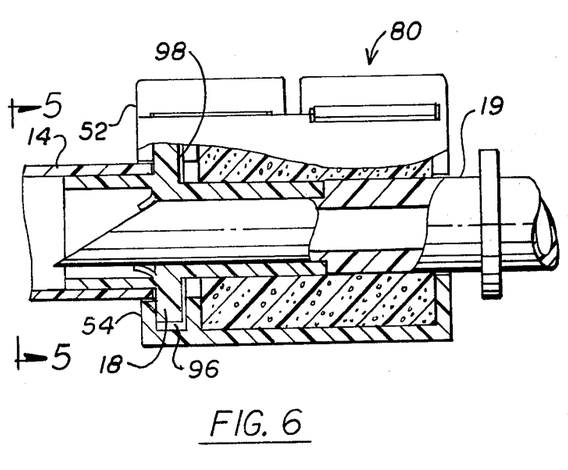
FIG. 6 of the drawings is a view in partial vertical section of the improved connecting device of FIG. 5.

In an alternative embodiment of the invention, as best seen in FIGS. 4-6, clasp member 80 is designed for one handed operation. In particular, latch mechanism 82 comprises first male member 84 and second male member 86 adapted for reception respectively, by first slot member 88 and second slot member 90. Clasp member 80 may be closed in a conventional manner. However, in order to re-open clasp 80, since each male and female slot member is oppositely disposed, converging digital pressure on first tab 92 and second tab 94, as seen in FIG. 5, causes latch mechanism 82 to disengage, thereby opening clasp 80.

FIG. 6 further illustrates the clasp of FIG. 4, in which end walls 52 and 54 are enclosed about port 14. Slots 96 and 98 are formed in C-shaped portions 38 and 40 and are adapted to receive circular rim 18, and to retain it therein. As a result, when piercing pin 19 is removed, clasp 80 will remain on port 14.

As best seen in FIGS. 7-11 of the drawings, in an alternative embodiment, clasp member 100 includes a first semicircular flange 102 (FIG. 8) extending from the distal end 104 of first substantially C-shaped body portion 38. A second semicircular flange 106 is of substantially the same size as first semicircular flange 102 and extends coaxially from distal end 108 of second substantially C-shaped body portion 40. First semicircular flange 102 and second semicircular flange 106 are positioned and constructed of the same size so as to meet upon closure of clasp member 100, thereby forming a tubular end port 110 (FIG. 9) extending from the distal end 104 of clasp member 100. Threading 112 extends helically around and is integrally formed on first semicircular flange 102 and second semicircular flange 106 so as to form a helical array about tubular end port 110. A mating lock 114 is positioned concentrically about tubular port 14 which extends from medical liquid container 12. Lock nut 114 is constructed and arranged for threaded engagement with the threading 112 on tubular end port 110. In addition, lock nut 114 is constructed, when rotated on end port 110, to come into abutment against circular flange 18. As a result, by means of clasp member 100, tubular port 14 and tubular piercing pin 19 may be fixedly connected.

Figure 10:
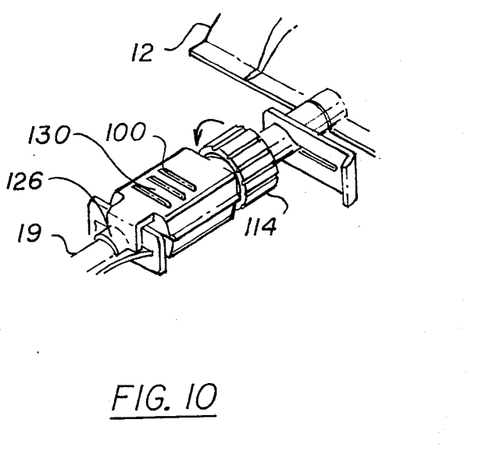
FIG. 10 of the drawings is a front perspective view of the connecting device of FIGS. 7-9 showing in particular a new bag and port assembly being threaddedly connected to the piercing pin and a new clasp member.
Figure 11:
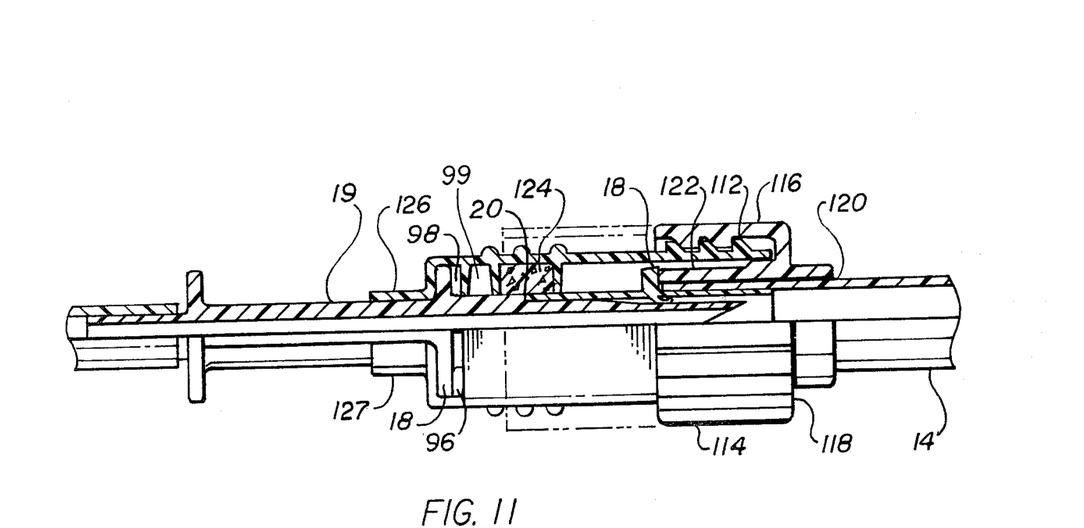
FIG. 11 of the drawings is a side view, partially broken away of the clasp member of FIGS. 7-10.

As best seen in FIG. 11 of the drawings, in one embodiment, lock nut 114 is formed as a cap having side wall 116 and end wall 118. A circular orifice 120 is formed in the center of lock nut 114 and is of the proper size for telescopic reception of tubular port 14. Lock nut 114 also includes iner rim 122 which is merely a tubular extension of orifice 120 into lock nut. Rim 122 is adapted for abutment against radial flange 18. Thus, as lock nut 114 is threadedly connected onto threading 112, further rotation is prevented by abutment against flange 18. At this point, tubular port 14 and piercing pin 19 are fixedly attached. Also seen in FIGS. 8-11 are port extensions 126 and 127 which extend from the proximal ends of C-shaped portions 38 and 40, and are adapted for enclosing a flange portion of piercing pin 19.

Along these same lines connector 100 includes both slots 96 and 98 for enclosure of flange 18, and annular slot 99 for preventing leakage of antiseptic solution.

Figure 8:
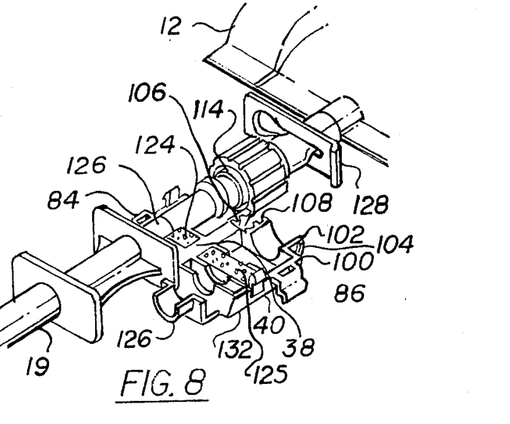
FIG. 8 of the drawings is a front perspective view of the connecting device of FIG. 7 showing in particular the clasp member in an open poistion.

As best seen in FIGS. 8 and 11, clasp member 100 preferably includes absorbent sponges 124 and 125 which contain an antiseptic solution such as povidone iodine. Absorbent sponge 124 is positioned within clasp member 100 for encirclement and enclosure of the connection between piercing pin 19 and tubular port 14.

Operation of the System of FIGS. 7-11

Figure 7:
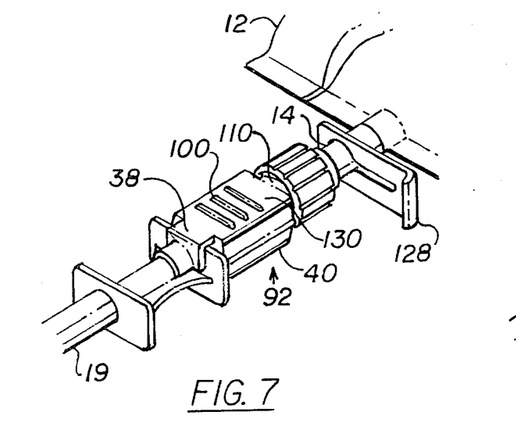
FIG. 7 of the drawings is a front perspective view of an alternative embodiment of the connecting device of FIGS. 1-6.

As seen in FIG. 7, piercing pin 19 and tubular port 14 are connected, with clasp member 100 closed about the connection therebetween. In a peritoneal dialysis system, dialysate is drained from the patient through the connection and into bag 12. When bag 12 is filled, slide clamp 128 is moved to a closed position as shown in FIG. 8. Clasp member 100 is then opened by means of latch mechanism 82, which comprises first female member 84 and first female member 86 being snapped open. Clasp 100 is then disposed of and a new clasp 100 is substituted therefor. Antiseptic sponges 124 and 125 may be preloaded with antiseptic solution or may have antiseptic solution dispensed therein prior to closure.

Figure 9:
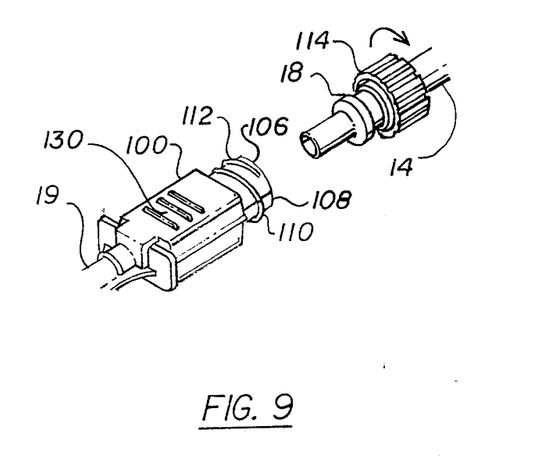
FIG. 9 of the drawings is a front perspective view of the connecting device of FIG. 7 showing the tubular port removed from the piercing pin and clasp member.

As best seen in FIG. 9, clasp 100 is then reclosed and tubular port 14 removed from connection with piercing pin 19. This is accomplished by means of counter-clockwise rotation of lock nut 14. A new bag of dialysate solution is then attached, as seen in FIG. 10 to piercing pin 19. Lock nut 14 is then rotated in a clockwise rotation and piercing pin 19 is used to penetrate the diaphragm 26 (not shown) within tubular insert 16. Dialysate is then allowed to flow through port 14, piercing pin 19 and into the patient. Once bag 12 is emptied, it is rolled up and carried by the patient.

In a preferred embodiment, clasp member 100, as well as clasp member 36, is constructed of a clear, or translucent thermoplastic material such as acrylic. Alternatively, other thermoplastic materials such as polypropylene, polyethylene, acrylonitrile butadiene stryene, and polycarbonate may be utilized. Piercing pin 19 and tubular port 14 are constructed of conventional medical solution container plastics such as polyvinyl chloride, polyethylene, teraphthalate, etc.

As best seen in FIGS. 7, 9 and 10, in a preferred embodiment, clasp member 100 includes one or more flat or planar surfaces such as surface 130. Surface 130 is flat in order to facilitate manipulation of clasp member 100 into an opened or closed position. Planar surface 130 is a portion of first substantially C-shaped section 38. Correspondingly, in order to facilitate manipulation, second substantially C-shaped portion 40 may have a planar surface 132. Thus, surfaces 130 and 132 can be pinched together in order to lock the device, even by those incapacitated through old age, failing eyesight or impeded motor skills.

Figure 12:
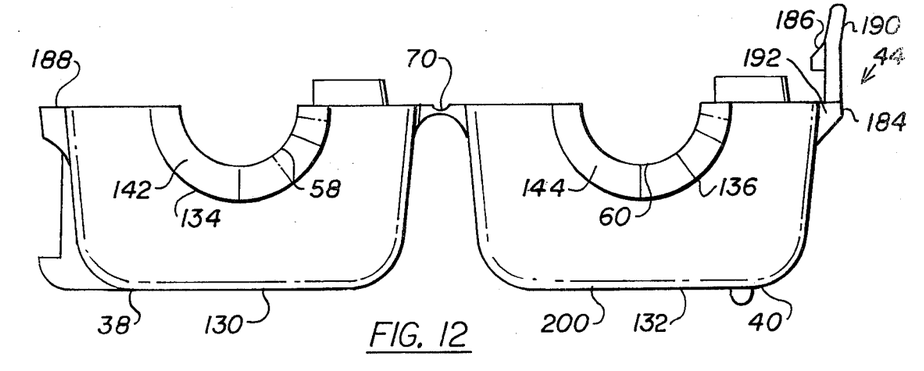
FIG. 12 of the drawings is a side view of an alternative embodiment of a clasp member for use with a piercing pin and tubular port.
Figure 13:
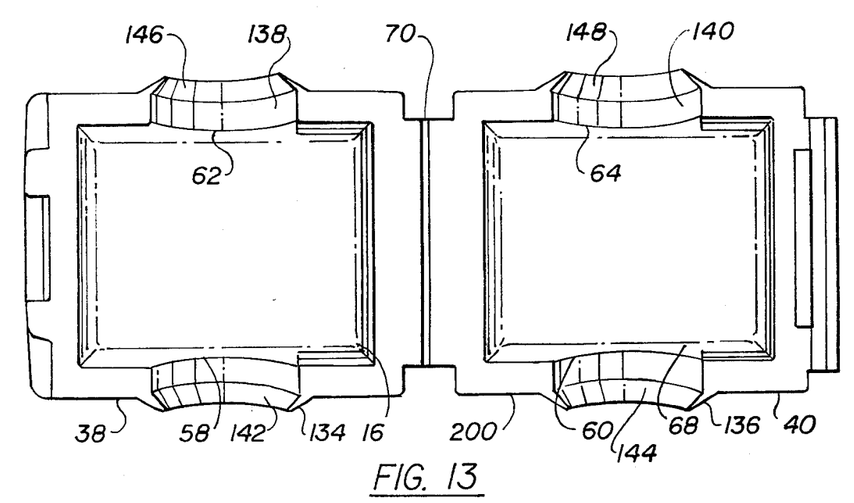
FIG. 13 of the drawings is a top view of the clasp member of FIG. 12.

Turning to FIGS. 12 and 13 of the drawings, an additional, alternative embodiment may be found in clasp member 200. Clasp member 200 is formed in substantially the same manner as clasp 36 and clasp 100, that is, first substantially C-shaped portion 38 and second substantially C-shaped portion 40 are hingedly connected on axis 70. Substantially planar surfaces 130 and 132 on body portion 38 and on body portion 40 are also shown. However, clasp 200 includes antileak skirts 134, 136, 138 and 140 extending from, respectively, semicircular slots 58, 60, 62 and 64. Antileak skirts 134, 136, 138 and 140 are formed on the outside surface of clasp 200 to enclose flanges 18 and 21 of piercing tubular port 14 and pin 19, respectively. Antileak skirts 134, 136, 138 and 140, as shown, taper from their original diameter to a smaller diameter. Tapered rim members 142, 144, 146 and 148, integrally formed about semicircular slots 58, 60, 62 and 64 and extend from clasp member 200. They are designed to retard the passage of antiseptic solution from sponge members 66 and 68 by means of surface tension and gravity within clasp member 200. Tapered rim portions 142, 144, 146 and 148 as shown, are integrally formed in the side walls of clasp 200.

Figure 14:
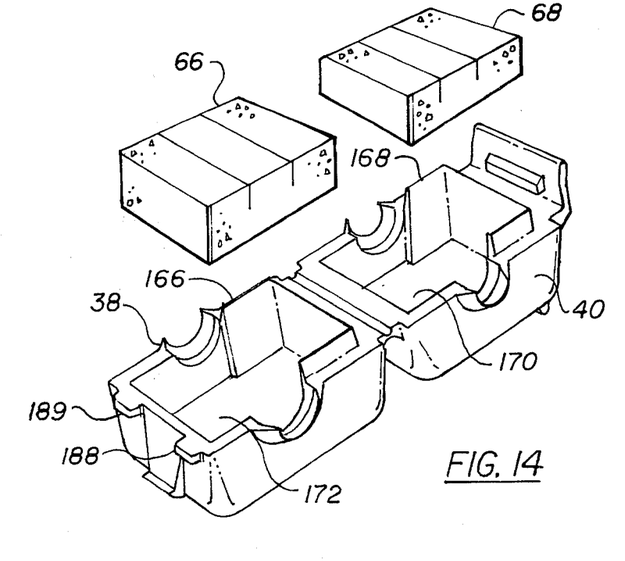
FIG. 14 of the drawings is a front perspective view of the clasp member of FIGS. 12 and 13 showing in particular antileak flanges and antileak skirts integrally formed in the clasp member and abosrbent sponge means adapted for insertion into the clasp member.

As best seen in FIG. 14, in a preferred embodiment, clasp member 200 also includes antileak flanges 166 and 168 integrally formed in the interior of first substantially C-shaped body portion 38 and second substantially C-shaped body portion 40. Flanges 166 and 168, as shown, are beveled rectangular rims which extend from each body portion and are designed for overlapping engagement with the corresponding openings 170 and 172 in opposite body portions 40 and 38 respectively. As a result, when body portion 38 and body portion 40 are hingedly pivoted closed, antiseptic solution contained within absorbent sponges 66 and 68 is prevented from leaking from clasp 200.

Figures 15, 16, 16A:
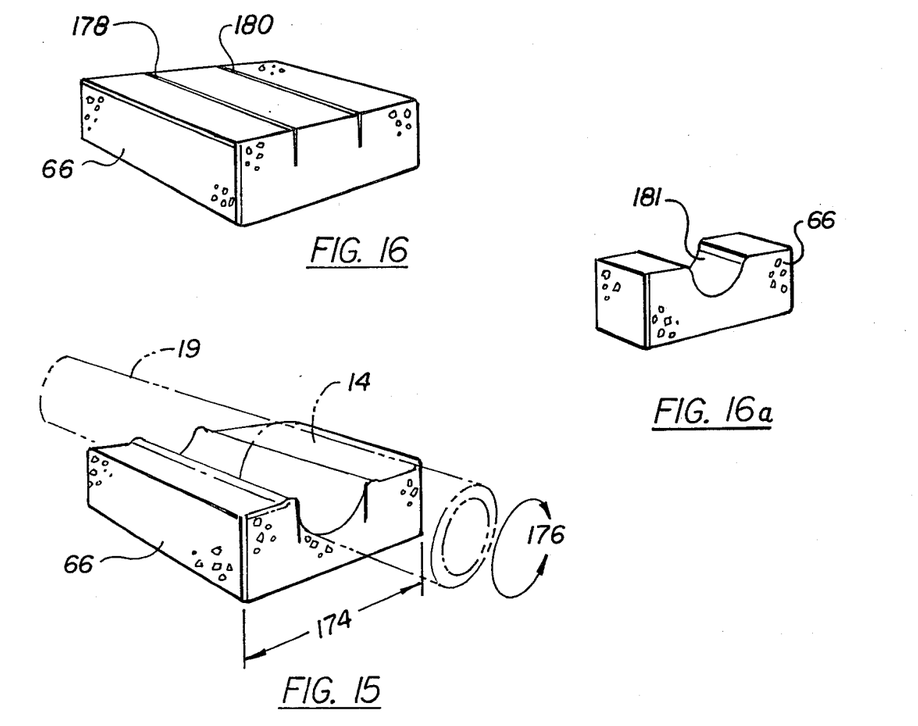
FIG. 15 of the drawings is a front perspective view of the sponge member shown in FIG. 14 showing in particular slits formed in the sponge member encompassing the connection between th tubular pin and tubular port of a CAPD system.
FIG. 16 of the drawings is a front perspective view of the sponge member of FIG. 15 showing in particular the aforementioned slits.
FIG. 16a of the drawings is a front perspective view of an alternate embodiment of the sponge member shown in FIG 15, showing in particular a sponge with a die cut slot for receiving the aforementioned tubular pin and port.
Figure 17:
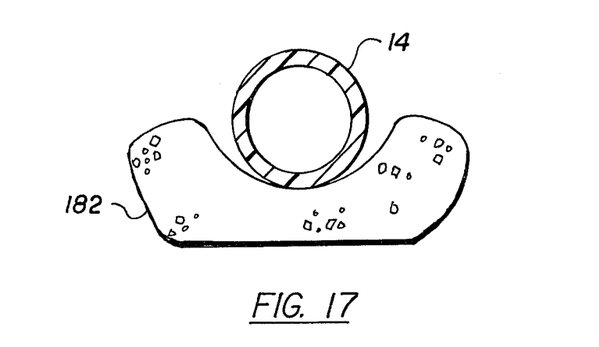
FIG. 17 of the drawings is a front cutaway view of a tubular port compressed against a sponge member without slits or die cutting.

As further seen in FIGS. 15, 16 and 17 of the drawings, in a preferred embodiment, absorbent sponge member 66 (and sponge member 68 which is of the same configuration) are equal in width 174 to one-half the circumference 176 of tubular port member 14 and tubular piercing pin 19. As a result, sponge member 66 (and sponge member 68) encompass and enclose the connection between tubular port member 14 and hollow piercing pin 19. Consequently, the sponge members maintain the aseptic condition of the connection.

As further seen in FIGS. 15 and 16, in a preferred embodiment, absorbent sponge member 66 (and sponge member 68) include a plurality of longitudinal slits 178 and 180 which are incorporated therein. Slits 178 and 180 allow tubular piercing pin 19 and port 14 to be substantially enclosed by absorbent sponge member 66. Alternatively, a die cut groove 181 may be formed in sponge member 66 (and sponge 68) which is rigid to accommodate piercing pin 19 and port 14. As seen in FIG. 17 of the drawings, in sponge member 182, which does not contain slits, tubular port 14 is not completely enclosed by sponge member 182 when compressed thereon.

Figure 18:
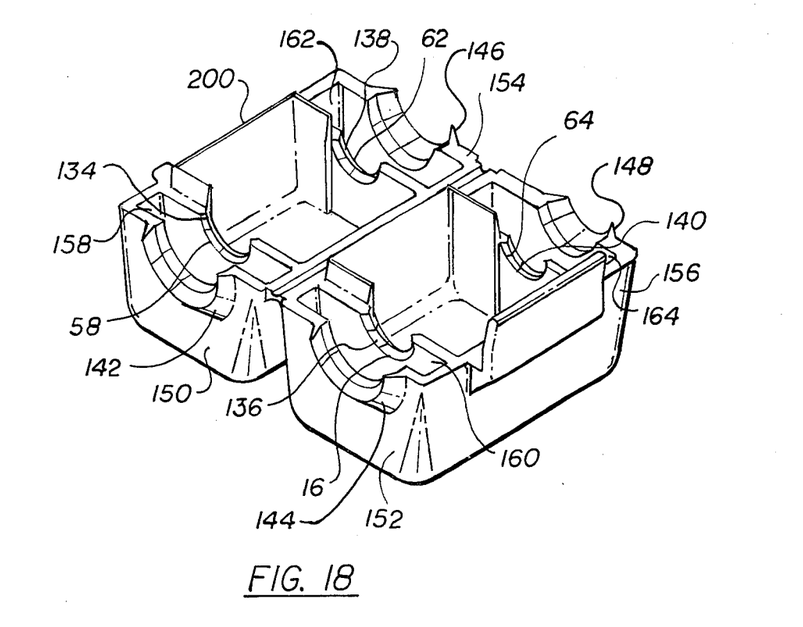
FIG. 18 of the drawings is a rear perspective view of an additional alternative embodiment of the clasp member previously described, showing in particular antileak shirts in the form of cowlings affixed to the ends of the clasp.
Figure 19:
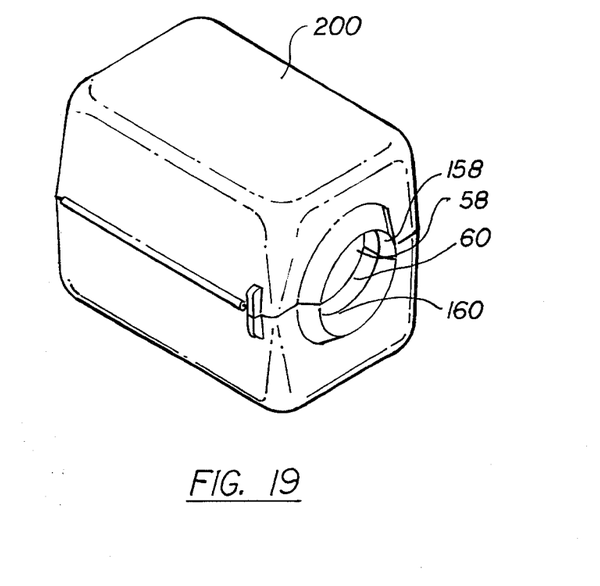
FIG. 19 of the drawings is a front perspective view of the clasp member of FIG. 18 showing in particular the clasp member in a closed configuration.

As seen in FIG. 18, antileak skirts 134, 136, 138 and 140 may also include cowlings 150, 152, 154 and 156 which extend from the respective side walls of clasp member 200 and are coaxially disposed about semicircular slots 58, 60, 62 and 64, respectively. Cowlings 150, 152, 154 and 156 are constructed so as to enclose either hollow tubular piercing pin 19 or tubular port 14 when clasp member 200 is closed. Included in the aforementioned cowlings are annular slots 158, 160, 162 and 164 which are positioned respectively. These annular slots receive excess solution discharged from sponge members 66 and 68, and retain it therein so as to prevent spillage from clasp member 200.

Returning to FIG. 12 of the drawings, in a preferred embodiment of clasp member 200, latch mechanism 44 comprises a pivotable tab 184 integrally formed in and extending from second substantially C-shaped body portion 40. Pivotable tab 184 has a lug 186 extending vertically therefrom which is constructed and arranged for mating engagement with the corresponding lug 188 on first substantially C-shaped body portion 38. Tab 184 also includes a lever arm 190 extending oppositely from lug 186, and a hinge 192 integrally formed therein, and positioned between lug 186 and lever arm 190. As a result, tab 184 may be released from lug 188 by the force of a single finger or digit against lever arm 190, thereby opening clasp 200 as required. Conversely, lug 186 and corresponding lugs 186 and 188 allow clasp 200 to be snapped closed in a relatively easy manner.

Figure 20:
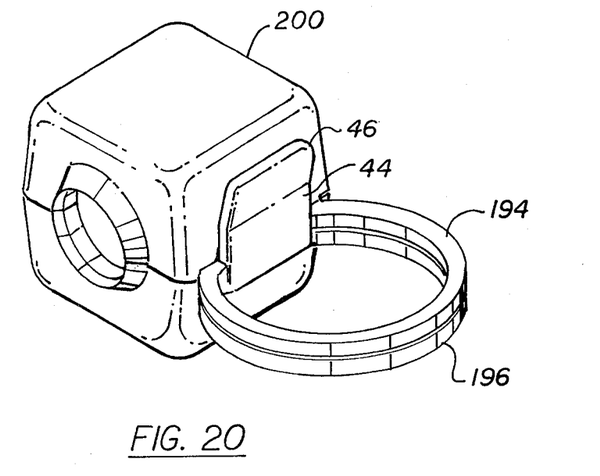
FIG. 20 of the drawings is a rear perspective view of an additional alternative embodiment of a clasp member, showing in particular a ring pull mechanism for opening the clasp member.
Figure 21:
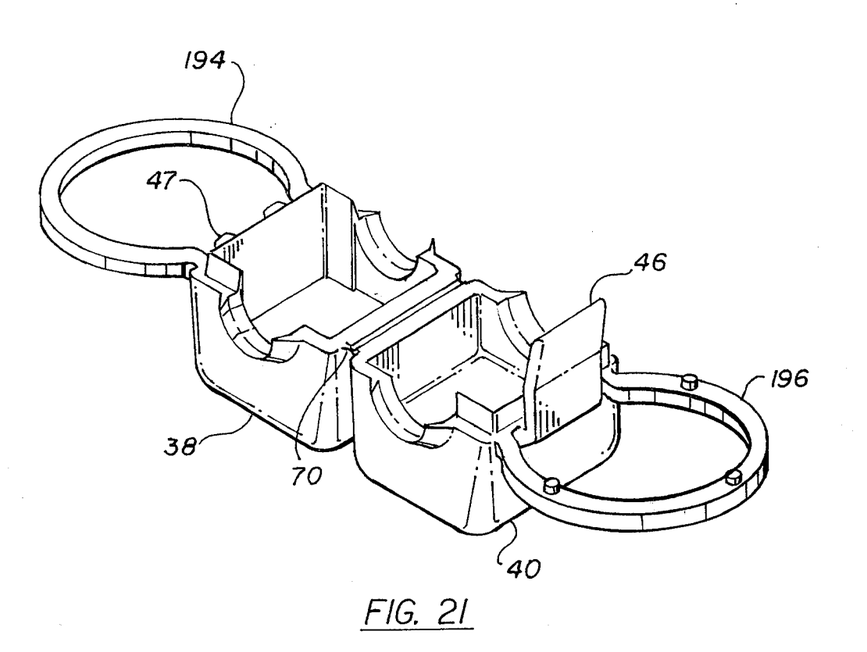
FIG. 21 of the drawings is a rear perspective view of the clasp member of FIG. 20 showing in particular the clasp in a open position.
Figure 22:
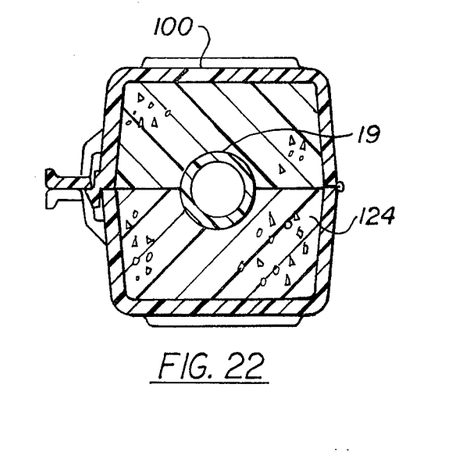
FIG. 22 of the drawings is a vertical section of the connecting device shown in FIGS. 7-11.
Figure 23:
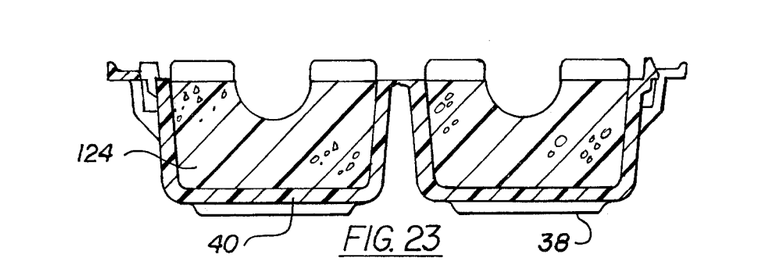
FIG. 23 of the drawings is a vertical section of the connecting device of FIG 22, shown in an open configuration.

As best seen in FIGS. 20 and 21, in an alternative embodiment of the invention, clasp member 200 includes latch mechanism 44 in the form of male member 46 on second body portion 40 and lugs 47 on first body portion 38. However, in addition to the embodiments, clasp member 200 also includes flexible ring portions 194 and 196 extending oppositely from first body member 38 and second body member 40 at opposing ends thereof. Thus, clasp member 200 may be joined in the conventional, previously described manner of hingedly closing body portions 38 and 40, or clasp member 200 may be closed by grasping ring members 194 and 196 and pivoting them together by means of hinge 70. Conversely, when opening of clasp member 200 is desired, ring members 194 and 196 may be separated and pulled apart so as release latch 44.

Figure 24:
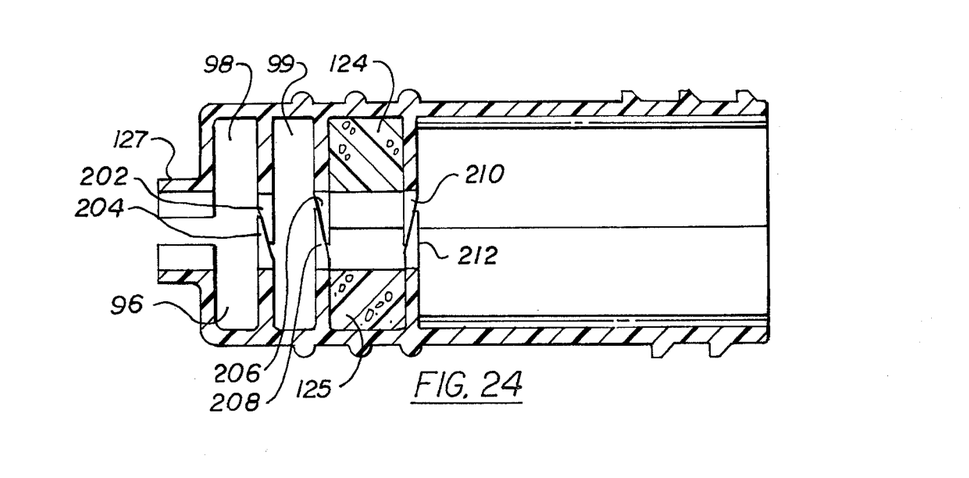
FIG. 24 of the drawings is a vertical section of the connecting device shown in FIG. 11.

As best seen in FIG. 24 of the drawings, beveled antileak flanges 202, 204, 206, 208, 210 and 212 are formed in the embodiment of connector 100 shown. Flanges 202, 206 and 210 slidingly mate against sealed flanges 204, 208 and 212, respectively, when C-shape portion 40 is pivoted close against C-shape section 38. As a result, antiseptic solution contained within sponges 124 and 125 is retarded from leaking out of connector 100.

The foregoing description and drawings merely explain and illustrate the invention, and the invention is not limited thereto, except insofar as the appended claims are limited to those skilled in the art who have the disclosure before them and are able to make modifications and variations therein without departing from the scope of the invention.

I claim:

1. An aseptic covering device for the connection between the tubular port of a medical liquid container and a piercing pin comprising:
   a clasp member comprising first and second substantially C-shaped body portions hingedly connected to each other and further including latching means at opposing ends thereof; said clasp member being constructed and arranged for the pivotal enclosure of said connection between said medical liquid container and said piercing pin;
   a plurality of absorbent sponge members containing an antiseptic solution disposed within each of said substantially C-shaped portions constructed and arranged for asepticizing the connection between said tubular port and said piercing pin;
   a coaxial tubular end port extending distally from said clasp member and having helically arranged threading disposed thereon; and
   lock nut means coaxially disposed about said tubular port member, constructed and arranged for threaded engagement with said threading means on said tubular end port of said clasp member so as to fixedly attach said tubular port to said clasp member and said piercing pin.

2. The connecting device as described in claim 1 and further comprising a rigid tubular insert member fixedly attached within and sealing said tubular port member, said rigid tubular insert member having a flange extending radially therefrom, adapted for limiting the insertion of said rigid tubular insert member into said tubular port member, with said pierceable diaphragm being integrally formed and positioned with said rigid tubular insert member.

3. The connecting device as disclosed in claim 1 wherein said tubular port member includes a flange member disposed about its distal end adapted for engagement with said locking means.

4. The connecting device as disclosed in claim 1 wherein said hollow tubular piercing pin includes a flange member extending therefrom adapted for engagement with said locking means.

5. The connecting device as disclosed in claim 2 or 3 or 4 wherein said clasp member is constructed and arranged for reception of and engagement with one or more of said flange members so as to fixedly position said connecting device therein.

6. The connecting device as disclosed in claim 1 wherein said antiseptic solution comprises povidone iodine.

7. The connecting device of claim 1 wherein said clasp member comprises a modular thermoplastic unit having an integrally formed flexible hinge between said first and second portions, integrally formed latch members oppositely disposed on said first and second portions, and integrally formed tabs for facilitating selective digital closure and opening of said connecting device.

8. The connecting device as disclosed in claim 1 wherein said latching means comprises;
   a first male member extending from said first C-shaped portion,
   said first male member being constructed and arranged for mating engagement with and interlocking to a first slot member disposed on said second substantially C-shaped portion;
   a second male member extending from said second substantially C-shaped member, said second male member being constructed and arranged for mating engagement with and interlocking to a second slot member disposed on said first substantially C-shaped member; and
   first and second tab means juxtaposed on opposite ends of said clasp member, said tab means being constructed and arranged for effecting selective engagement or disengagement of said latching means when digital force is applied concurrently on said first and second tab means so as to direct said tabs toward or away from each other.

9. The connecting device as disclosed in claim 1 wherein said latch means comprises a pivotable tab integrally formed and extending from said second substantially C-shaped body portion, said pivotable tab having a lug extending therefrom constructed and arranged for mating engagement with a corresponding lug on said first substantially C-shaped body portion, a lever arm oppositely extending therefrom and a hinge between said lug and said lever arm so as to allow single digit opening of said clasp, as required, and conversely facilitating snap closure thereof.

10. The connecting device as disclosed in claim 1 wherein said latch means comprises a plurality of ring members extending from first and second substantially C-shaped body members at opposing ends thereof and resilient first and second snap lock means at said opposing ends for selective joinder of said C-shaped members, said ring members being effective to facilitate pulling apart of said snap lock means and thereby opening of said clasp member.

11. An aseptic covering device for the connection between the tubular port of a medical liquid container and a piercing pin comprising:
 a clasp member comprising first and second substantially C-shaped body portions hingedly connected to each other and further including latching means at opposing ends thereof; said clasp members being constructed and arranged for the pivotal enclosure of said connection between said medical liquid container and said piercing pin;
 a plurality of absorbent sponge members containing an antiseptic solution disposed within each of said substantially C-shaped portions constructed and arranged for asepticizing the connection between said tubular port and said piercing pin;
 a first semicircular flange member coaxially extending from the distal end of said first substantially C-shaped body portion;
 a second semicircular flange member of substantially the same size as said first semicircular flange member and coaxially extending from the distal end of said second substantially C-shaped body portion;
 said first and second semicircular flange members being constructed and arranged to meet upon closure of said substantially C-shaped body, thereby forming a tubular end port from said clasp member;
 threading means integrally formed on and extending from said first and second semicircular flange members, constructed and arranged so as to form a helical array about said tubular end port from said clasp member; and
 lock nut means coaxially disposed about said tubular port member, constructed and arranged for threaded engagement with said threading means on said tubular end port of said clasp member thereby fixedly attaching said tubular port to said clasp member and said piercing pin.

12. The connecting device as disclosed in claim 11 wherein each of said substantially C-shaped portions includes a plurality of semicircular slots oppositely disposed thereon and adapted for reception and enclosure of said tubular port member and said flexible tubing.

13. The connecting device as disclosed in claim 1 or 11 wherein said clasp member comprises one or more planar surfaces integrally formed in and disposed on the outer surface or surfaces of said substantially C-shaped body portions and positioned so as to facilitate digital manipulation of said first and second substantially C-shaped members into a closed configuration.

14. The connecting device as disclosed in claim 1 or 11 and further comprising:
 antileak skirt means concentrically disposed about said semicircular slots, said antileak skirt means being constructed and arranged to retard the passage of antiseptic solution from said sponge member.

15. The connecting device as disclosed in claim 4 wherein said antileak skirt means comprises a tapered rim member integrally formed about and extending from each of said semicircular slots.

16. The connecting device as disclosed in claim 15 wherein said antileak skirt means comprises a plurality of cowling members, each of which is coaxially disposed about said semicular slots and is constructed and arranged to enclose either said hollow tubular piercing pin or said tubular port member, respectively; said cowling members further including an annular slot integrally formed therein, constructed and arranged to receive excess solution discharged from said sponge member.

17. The connecting device as disclosed in claim 1 or 11 and further comprising a plurality of antileak flange members integrally formed in the interior of said first and second substantially C-shaped body portions constructed and arranged for overlapping engagement with the opposing inside surface of a C-shaped body portion so as to substantially seal said clasp member when said first and second substantially C-shaped portions are joined.

18. The connecting device as disclosed in claim 1 or 11 wherein said absorbent sponge members are equal in width to one-half the circumference of said tubular port member, so as to encompass and enclose the connection between said tubular port member and said hollow tubular piercing pin, thereby maintaining the aseptic condition of same.

19. The connecting device as disclosed in claim 1 or 11 wherein said absorbent sponge members include a plurality of longitudinal slits incorporated therein constructed and arranged to facilitate enclosure of said connection.

20. A connecting device for medical liquid containers comprising:
 a tubular port member extending from the container;
 a pierceable diaphragm positioned within and sealing said tubular port member;
 a hollow tubular piercing pin connected at its proximal end to a length of flexible tubing and having a sharpened tip at its distal end adapted for penetration of said pierceable diaphragm member;
 locking means for the selective retention of said piercing pin within said tubular port member;
 said locking means comprising a clasp member including first and second substantially C-shaped body portions hingedly connected to each other and further including latching means at opposing ends thereof, said clasp member being constructed and arranged for the pivotal enclosure of said connecting device and fixed positioning therein;
 said clasp member further including a plurality of absorbent sponge members containing an antiseptic solution disposed within each of said substantially C-shaped portions constructed and arranged for asepticizing the connection between said tubular port and said piercing pin;
 a first semicircular flange member coaxially extending from the distal end of said first substantially C-shaped body portion;
 a second semicircular flange member of substantially the same size as said first semicircular flange member and coaxially extending from the distal end of said second substantially C-shaped body portion;

said first and second semicircular flange members being constructed and arranged to meet upon closure of said substantially C-shaped body, thereby forming a tubular end port from said clasp member;

threading means integrally formed on and extending from said first and second semicircular flange members, constructed and arranged so as to form a helical array about said tubular end port from said clasp member; and lock nut means coaxially disposed about said tubular port member, constructed and arranged for threaded engagement with said threading means on said tubular end port of said clasp member thereby fixedly attaching said tubular port to said clasp member and said piercing pin.

21. A method of aseptically sealing the connection between a piercing pin and the tubular port of a medical liquid container with a clasp member having a plurality of sponge members therein, saturated with antiseptic solution, said clasp member comprising: a first semicircular flange member coaxially extending from the distal end of said first substantially C-shaped body portion, a second semicircular flange member of substantially the same size as said first semicircular flange member and coaxially extending from the distal end of said second substantially C-shaped body portion, said first and second semicircular flange members being constructed and arranged to meet upon closure of said substantially C-shaped body, thereby forming a tubular end port from said clasp member, threading means integrally formed on and extending from said first and second semicircular flanges, constructed and arranged to as to form a helical array about said tubular end port from said clasp member, and locknut means coaxially disposed about said tubular port member, constructed and arranged for threaded engagement with said threading means on said tubular end port of said clasp member for fixed attachment of said tubular port to said clasp member and said piercing pin, comprising the steps of:

inserting said pin into said port;

piercing the diaphragm of said port with said pin;

enclosing the assembled port and pin within said clasp mechanism having a plurality of sponge members therein, saturated with antiseptic solution;

rotatably threading said lock nut means onto said threading means of said tubular end port until said lock nut means about said clasp member, thereby fixedly attaching said tubular port member to said tubular piercing pin.

* * * * *